US007018821B2

(12) United States Patent
Becker et al.

(10) Patent No.: US 7,018,821 B2

(45) Date of Patent: Mar. 28, 2006

(54) HIGHLY IMPACT-RESISTANT GRANULES

(75) Inventors: Nathaniel T. Becker, Hillsborough, CA (US); Mark S. Gebert, Pacifica, CA (US); Isabelle Mazeaud, San Francisco, CA (US)

(73) Assignee: Genencor International, Inc., Palo Alto, CA (US)

(*) Notice: Subject to any disclaimer, the term of this patent is extended or adjusted under 35 U.S.C. 154(b) by 0 days.

(21) Appl. No.: 10/176,342

(22) Filed: Jun. 20, 2002

(65) Prior Publication Data

US 2003/0129717 A1 Jul. 10, 2003

Related U.S. Application Data

(60) Provisional application No. 60/300,574, filed on Jun. 22, 2001.

(51) Int. Cl.
*C12N 9/98* (2006.01)
*C12N 11/14* (2006.01)
*C12N 11/10* (2006.01)
*C12N 11/08* (2006.01)

(52) U.S. Cl. ...................... 435/187; 435/176; 435/178; 435/180

(58) Field of Classification Search ................ 435/176, 435/178, 180, 187

See application file for complete search history.

(56) References Cited

U.S. PATENT DOCUMENTS

| | | | |
|---|---|---|---|
| 3,423,489 A | 1/1969 | Arens et al. | |
| 4,106,991 A | 8/1978 | Markussen et al. | |
| 4,123,206 A | 10/1978 | Dannelly | |
| 4,242,219 A | 12/1980 | Bogerman et al. | |
| 4,675,140 A | 6/1987 | Sparks et al. | |
| 4,689,287 A | 8/1987 | Katoh et al. | |
| 4,689,297 A | 8/1987 | Good et al. | |
| 4,760,025 A | 7/1988 | Estell et al. | |
| 4,876,198 A | 10/1989 | Markussen | |
| 5,034,324 A * | 7/1991 | Shinozaki et al. | 435/178 |
| 5,324,649 A | 6/1994 | Arnold et al. | |
| 5,739,091 A | 4/1998 | Kiesser et al. | |
| 5,879,920 A | 3/1999 | Dale et al. | |
| 6,035,716 A | 3/2000 | Beekman et al. | |

FOREIGN PATENT DOCUMENTS

| | | |
|---|---|---|
| WO | WO 90/09440 | 8/1990 |
| WO | WO 91/06637 | 5/1991 |
| WO | WO 92/06165 | 4/1992 |
| WO | WO 92/13030 | 8/1992 |
| WO | WO 98/03849 | 1/1998 |
| WO | WO 00/24877 | 5/2000 |
| WO | WO 01/25323 A1 | 4/2001 |

OTHER PUBLICATIONS

Sparks, Richard E., << Kirk-Othmer Encyclopedia of Chemical Technology >>, 3rd ed., vol. 15, 1981.

van Ee, Jan H. et al., ed., << Enzymes in Detergency >>, Marcel Dekker, Inc., New York, pp. 310-313, 1997.

Van Vlack, Lawrence H. << Elements of Material Science and Engineering >>, 4th ed.,Addison-Wesley, pp. 6-13, 1980.

Goodwin John T. et al., Vandegaer, Jan E., Ed., American Chemical Society Symposium on Microencapsulation *Processes and Applications Physical Methods for Preparing Microcapsul s, (1973 :Chicago) Plenum Press, New York.*

* cited by examiner

*Primary Examiner*—David M. Naff
(74) *Attorney, Agent, or Firm*—Genencor International, Inc.

(57) ABSTRACT

The present invention provides highly impact-resistant, water-soluble or water dispersible, low-dust granules comprising an active ingredient and methods for obtaining the same.

6 Claims, 5 Drawing Sheets

HIGHLY IMPACT-RESISTANT GRANULES

RELATED APPLICATIONS

This application claims priority to pending U.S. provisional application Ser. No. 60/300,574, filed on Jun. 22, 2001.

FIELD OF THE INVENTION

This invention relates to highly impact-resistant granules comprising an active ingredient, preferably an enzyme, and a flexible film formed from a polymeric material surrounding the active ingredient as well as processes for producing the granules and flexible film.

BACKGROUND OF THE INVENTION

Various industries, such as detergent manufacturing, pharmaceutical manufacturing, agrochemical manufacturing, and personal care manufacturing include compositions comprising active ingredients, particularly enzymes, that tend to form dust due to physical forces encountered during handling and blending operations. One of the problems with dust formation is that dust can cause health problems and allergic reactions. In an effort to protect the active ingredient and reduce dust formation, active ingredients have been formulated with various compounds including binders, coating agents, bleach-scavenging agents, and various encapsulating agents. Numerous techniques have been developed to produce these formulations including prilling, extrusion, spheronization, drum granulation, and fluid bed spray coating. (See e.g. U.S. Pat. No. 4,106,991; U.S. Pat. No. 4,242,219; U.S. Pat. No. 4,689,297; and U.S. Pat. No. 5,324,649).

However, prior art formulations, which produce particles or granules including an active ingredient, do not always exhibit sufficient impact resistance during handling and as a result form dust when typical physical forces are encountered during handling.

SUMMARY OF THE INVENTION

One aspect of the invention is a highly impact-resistant granule comprising an impact-sensitive particle including an active ingredient and surrounding said impact-sensitive particle a film comprising a polymer, the film having an elongation upon break of at least 30% and comprising less than about 20% by weight of the highly impact-resistant granule, wherein said impact-sensitive particle has more than about 10% mass attrition and said highly impact-resistant granule has less than about 5% mass attrition. In a preferred embodiment of this aspect, the film includes a polymer selected from the group consisting of polyvinyl alcohol (PVA), gelatin, and modified starch, such as hydroxypropylated corn starch, cellulose ethers and derivatives and copolymers thereof, particularly PVA. In another preferred embodiment of this aspect, the film further includes a plasticizer selected from the group consisting of glycerol, propylene glycol, polyethylene glycol, a sugar, and a sugar alcohol. In yet another embodiment, the film includes PVA, glycerol and a gelling agent. Preferably, the active ingredient is a protein or peptide, preferably an enzyme selected from the group consisting of proteases, cellulases, amylases, lipases, cutinases and combinations thereof. The active ingredient may be incorporated into the core of the granule or preferably the active ingredient is layered over the core.

In another aspect, the invention relates to a method for producing highly impact-resistant granules comprising: preparing the water soluble or water dispersible film coating composition, obtaining a core material and active ingredient wherein the active ingredient is either incorporated into the core or in a layer surrounding the core; casting the flexible film composition onto the core material including the active ingredient; and obtaining a granule wherein the flexible film comprises about 20% or less by weight of the granule and said granule has an Repeated Impact Test (RIT) dust value of less than about 100,000 ng/g.

In a preferred embodiment of the method, the active ingredient is an enzyme, particularly an enzyme selected from the group of proteases, cellulases, amylases, cutinases, lipases and combinations thereof; the polymer is PVA and optionally glycerol is included as a plasticizer. In another aspect of the invention, a gelling agent is added as a component of the flexible film.

Another aspect of the invention relates to the use of the highly impact-resistant granules according to the invention to deliver active ingredients to an aqueous environment such as detergent active ingredients in a wash water.

In a further aspect the invention relates to compositions comprising the highly impact-resistant granules according to the invention.

DETAILED DESCRIPTION OF THE INVENTION

Figure 1:
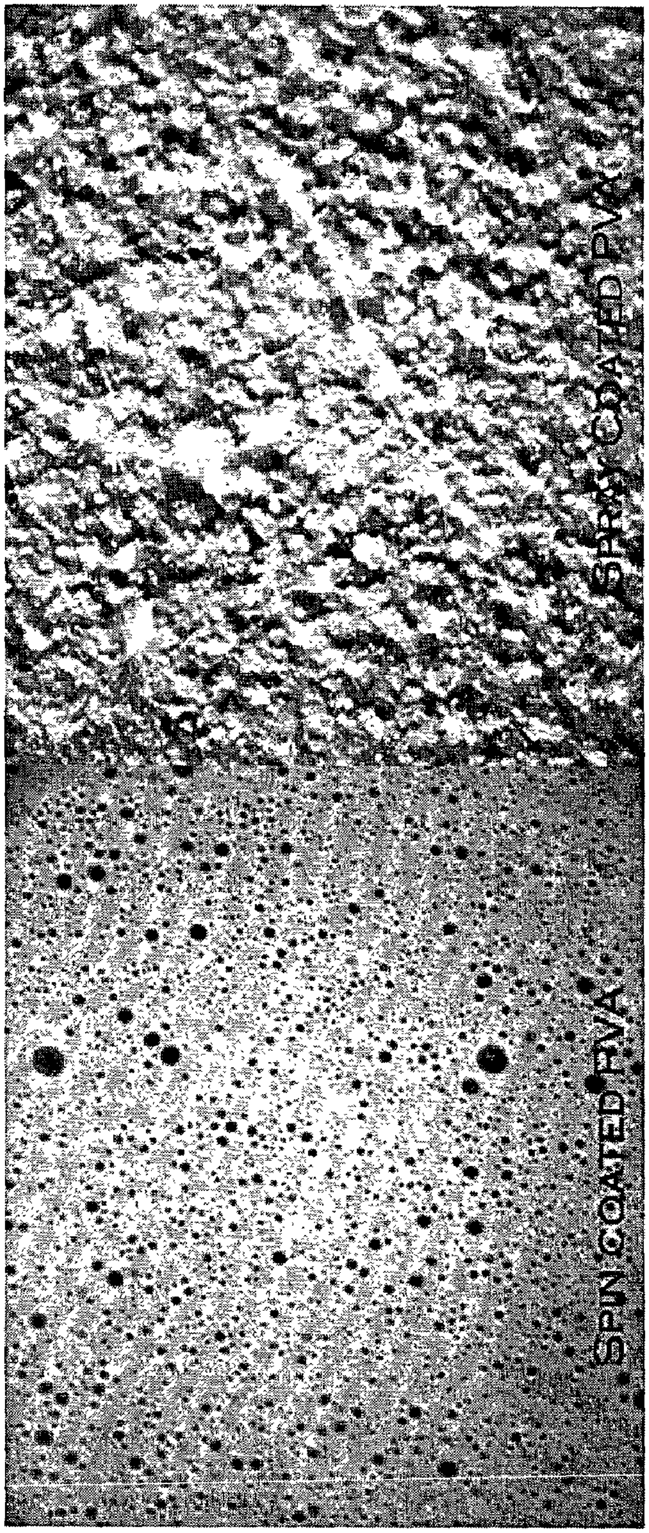
FIG. 1 is a comparison microscopic view at ×4 magnification of a spin coated flexible film of the present invention and a spray coated flexible film.

The present inventors have found that a granule comprising a flexible film having specific properties and applied in a specific manner to a particle comprising a core, which may include an active ingredient incorporated therein or which may be surrounded by a layer including an active ingredient, can impart impact resistance to the particle. This results in a granule with reduced potential for dust formation because it is less subject to unwanted breakdown from impact forces during handling. The granules of the present invention are highly impact-resistant granules which are made to deliver an active ingredient incorporated therein, particularly to an aqueous environment. The granules of the invention are very useful, for example in cleaning products, particularly detergent products, personal care products, fabric care products, and pharmaceutical products.

Unless defined otherwise, all technical and scientific terms used herein have the same meaning as commonly understood by one of ordinary skill in the art to which this invention pertains. As used in the specification and claims, the singular “a”, “an” and “the” include the plural references unless the context clearly dictates otherwise. For example, the term granule may include a plurality of granules.

A highly impact-resistant granule according to the invention is defined as a granule which exhibits less than 10%, less than 9%, less than 8%, less than 7%, less than 6%, less than 5%, less than 4%, less than 3%, less than 2% and/or less than 1% mass attrition as measured by a Repeated Impact test Device (RIT) at 216,000 collisions at 8.7 m/s and an amplitude of 1.5 cm (See U.S. Pat. No. 6,035,716). Alternatively, a highly impact-resistant granule according to the invention may be defined by the complementary value for mass retained, instead of the mass lost (attrition) as described above, in which case a highly impact-resistant granule is one which retains between about 90% to 100% of its original mass. For example, RIT mass retention is at least about 90%, at least about 92%, at least about 93%, at least about 95%, and at least about 96% of its original mass when subjected to 216,000 collisions at 8.7 m/s and an amplitude of 1.5 cm. (See U.S. Pat. No. 6,035,716). Mass retained is equal to 100% minus the attrition value.

The term attrition as used herein includes breakdown of a granule within a process, and includes abrasion and fragmentation.

An impact-sensitive particle or granule may be defined as one that exhibits a mass attrition in the range of about 10% to about 100%; more preferably a mass attrition of about 10%, about 15%, about 20%, about 30% or more. An impact-sensitive particle or granule may exhibit a mass attrition greater than 50%.

The term "elongation upon break" is a property of the polymer comprising the flexible film herein. Elongation upon break is defined as the maximum tensile strain or deformation which can be applied to a film prior to breakage or failure. It is expressed as the percentage increase in length relative to the original length or gage length of a film sample prior to the application of tensile stress. Percent elongation depends on the gage length and is the increase in gage length measured after failure divided by the original gage length. Failure of the film is considered the point at which the film breaks. For the purpose of this invention a gage length of 50 mm is commonly used, although a gage length of 10 to 100 mm may also be used. A 30 mm gage length was used in the elongation measurements for the examples illustrated herein. For a discussion of elongation upon break and gage length, reference is made to L. Van Vlack, "Elements of Material Science and Engineering, 4th Ed. Addison-Wesley Publishing Company, 1980, pages 6–13.

A "film elastic modulus", "Young's modulus" or "modulus" is calculated from the stress or strain mechanical tests known in the art and is defined as the rate of change of strain as a function of stress. It is the slope of the initial linear portion of a stress-strain diagram and is also referred to as the stress-strain ratio. Film tensile strength is defined herein as the maximum strength of a material subjected to tensile loading; the maximum tensile stress which can be applied in a tension test prior to breakage or failure.

Granules

The granules according to the invention comprise an active ingredient and further a flexible film surrounding the active ingredient. The active ingredient may be incorporated into a core or may be layered around the core followed by a layer of the flexible film. While not meant to limit the invention, the granule is preferably comprised of from about 80 to 99% core, about 0.01 to 50% active ingredient, and about 1 to 20% flexible film by weight.

The granules of the invention are highly impact-resistant and exhibit low dust, particularly ultra low dust, as defined herein. The granules are stable when stored under ambient humidity and temperature conditions, but soluble or dispersible upon contact with water so as to release the active ingredient or part thereof upon contact with water. Preferred granules have a mean granule size in the range of about 50 to 4000 microns, also about 100 to 2500 microns, about 150 to 1500 microns, and even about 200 to 800 microns.

Several industrial tests have been developed to measure the mechanical resistance to attrition and dusting formation of different granular enzyme formulations. These include the Heubach attrition test and the elutriation test. The Heubach test subjects particles to defined crushing and fluidization forces by using rotating paddles to roll steel balls through a bed of granules contained within a cylindrical chamber and simultaneously percolating a stream of air through the bed to strip off any dust that is generated. The generated dust is drawn by vacuum through a tube and deposited onto a filter pad outside the Heubach chamber. The weight or active component of the dust collected is referred to as Heubach dust. In the elutriation test, granules are placed on a glass frit within a tall glass tube and fluidized with a constant dry airstream over a fixed period of time. A discussion of the principles, operation and limitations of the Heubach and elutriation dust tests can be found for example, in "Enzymes In Detergency" ed. Jan H. van Ee., Ch. 15, pgs. 310–312, (Marcel Dekker, Inc. New York (1997) and references cited therein.

While the Heubach and elutriation tests are in common usage, neither of these tests adequately models the isolated effect of impact forces upon granule integrity and attrition. For purposes of modeling attrition of particles caused by impact forces, particularly the effects of large numbers of repeated impacts of defined magnitude, the Repeated Impact Test (RIT) was developed. In this test a sample of granules is vibrated at a controlled frequency and amplitude within a chamber. The amount of damaged particles or fragments (RIT mass attrition) is measured, or after removing all the granules and broken granule fragments the dust generated (RIT dust) is extracted from the box with a buffer and assayed for enzyme activity (See WO 98/03849 and U.S. Pat. No. 6,035,716 which are incorporated by reference herein).

Highly impact-resistant granules of the invention tend to be resistant to the high velocity impact forces and often as well to slow compression forces typically encountered in various manufacturing operations, although the specific mode of failure under the slow strain rate of compression can be quite different than that seen with the high strain rate of high velocity impact. For example, the granules are resistant to velocities greater than 1 m/s, 3 m/s, 5 m/s and even 10 m/s or greater. By utilizing the flexible film according to the invention, the resulting granules are well suited to readily absorb substantial and repeated impacts. The flexible film coating tends to deform while maintaining its integrity absorbing applied energy without reaching a point of sudden failure.

As measured by the RIT dust test, a highly impact-resistant granule has an enzyme dust level of less than 200,000 ng/g and preferably less than about 100,000 ng/g. An ultra low enzyme dust level is less than about 3000 ng/g, preferably less than 2000 ng/g. Preferred highly impact resistant granules have less than 10% mass attrition measured by RIT.

It is a key and surprising feature of this invention that a relatively small amount of a flexible film coating, constituting a minor percentage of the final granule, is sufficient to absorb the energy of impact, so long as it has sufficient flexibility as defined herein (See FLEXIBLE FILM section). It also is surprising that the same materials used to make the flexible film coating do not produce an impact resistant granule when used to form the core of the granule as opposed to a flexible film coating for the granule.

The flexible film coating of the present invention has the advantage of being able to convert otherwise impact sensitive granules or cores into impact resistant particles, with a modest amount of additional material and processing. It is therefore not necessary to completely re-engineer or reformulate a granule to make it impact resistant. It is a further advantage of this invention that converting impact-sensitive granules to impact-resistant granules does not diminish desirable properties such as ease of production, handling, solubility, enzymatic stability, thermal stability, and resistance to water pickup during storage in humid conditions.

Cores

The core is the inner nucleus of the granule, and is characterized as an impact-sensitive particle. Suitable cores for use in the present invention are preferably of a highly hydratable material (i.e., a material which is readily dispersible or soluble in water). The core material should either disperse in water (disintegrate when hydrated) or solublize in water by going into a true aqueous solution. Clays (bentonite, kaolin), nonpareils and agglomerated potato starch are considered dispersible. Nonpareils are spherical particles consisting of a seed crystal that has been built onto and rounded into a spherical shape by binding layers of powder and solute to the seed crystal in a rotating spherical container. Nonpareils are typically made from a combination of a sugar such as sucrose, and a powder such as cornstarch. Alternate seed crystal materials include sodium chloride or sodium sulfate seeds and other inorganic salts which may be built up with ammonium sulfate, sodium sulfate, potassium sulfate and the like.

Granules composed of inorganic salts and/or sugars and/or small organic molecules may be used as the cores of the present invention. Suitable water soluble ingredients for incorporation into cores include: sodium chloride, ammonium sulfate, sodium sulfate, urea, citric acid, sucrose, lactose and the like. Water-soluble ingredients can be combined with water dispersible ingredients. Cores of the present invention may further comprise one or more of the following: active ingredients, polymers, fillers, plasticizers, fibrous materials, extenders and other compounds known to be used in cores. Suitable polymers include—polyvinyl alcohol (PVA), polyethylene glycol, polyethylene oxide, and polyvinyl pyrrolidine. The PVA may be partially hydrolyzed (70–90%); intermediately hydrolyzed (90–98%); fully hydrolyzed (98–99%); super hydrolyzed (99–100%) PVA, or a mixture thereof, with a low to high degree of viscosity.

Suitable fillers useful in the cores include inert materials used to add bulk and reduce cost, or used for the purpose of adjusting the intended enzyme activity in the finished granule. Examples of such fillers include, but are not limited to, water soluble agents such as urea, salts, sugars and water dispersible agents such as clays, talc, silicates, carboxymethyl cellulose and starches.

Suitable plasticizers useful in the cores of the present invention are nonvolatile solvents added to a polymer to reduce its glass transition temperature, thereby reducing brittleness and enhancing deformability. Typically, plasticizers are low molecular weight organic compounds and are highly specific to the polymer being plasticized. Examples include, but are not limited to, sugars (such as, glucose, fructose and sucrose), sugar alcohols (such as, sorbitol, xylitol and maltitol) polyols (polyhydric alcohols for example, alcohols with many hydroxyl radical groups such as glycerol, ethylene glycol, propylene glycol or polyethylene glycol), polar low molecular weight organic compounds, such as urea, or other known plasticizers such as dibutyl or dimethyl phthalate, or water.

Suitable fibrous materials useful in the cores of the present invention include materials which have high tensile strength and which can be formed into fine filaments having a diameter of 1 to 50 microns and a length equal to at least four diameters. Typical fibrous materials include, but are not limited to: cellulose, glass fibers, metal fibers, rubber fibers, azion (manufactured from naturally occurring proteins in corn, peanuts and milk) and synthetic polymer fibers. Synthetics include Rayon®, Nylon®, acrylic, polyester, olefin, Saran®, Spandex® and Vinal®. Typically cellulose fibers have an average fiber length of 160 microns with a diameter of about 30 microns.

Cores can be fabricated by a variety of granulation techniques well known in the art including: crystallization, precipitation, pan-coating, fluid-bed coating, rotary atomization, extrusion, spheronization, drum granulation and high-shear agglomeration.

In one embodiment of the present invention, the core is a water-soluble or dispersible nonpareil (either sugar or salt as described above) which can be further coated by or built up from the seed crystal (nonpareil) using polyvinylalcohol (PVA) either alone or in combination with anti-agglomeration agents such as titanium dioxide, talc, or plasticizers such as sucrose or polyols. The level of PVA in the coating of the nonpareil may represent from about 0.5% to 20% of the weight of the coated nonpareil.

The core of the granules of the present invention, including all active ingredients and coatings, other than the flexible film coating on such core material as described above, preferably comprises between about 80 to 99%, and about 90 to 99% by weight of the granule. In general, the core including any active ingredient incorporated therein is an impact-sensitive particle. However, the invention is not limited by the type of core, and numerous patents and publications describe cores that may be used in the invention and reference is made to U.S. Pat. No. 5,879,920; U.S. Pat. No. 4,689,287 and WO 0024877.

Active Ingredients

The active ingredient may be any material which is to be added to a granule. The active ingredient may be a biologically viable material, an agrochemical ingredient, such as a pesticide, fertilizer or herbicide; a pharmaceutical ingredient or a cleaning ingredient. In a preferred embodiment, the active ingredient is an enzyme, protein, peptide, bleach, bleach activator, perfume, vitamin, hormone or other biologically active ingredient.

Most preferred active ingredients are one or more enzymes. A nonlimiting list of enzymes include proteases, cellulases, lipases, cutinases, oxidases, transferases, reductases, hemicellulases, amylases, esterases, isomerases, pectinases, lactases, peroxidases, laccases and mixtures thereof. Preferred enzymes include those enzymes capable of hydrolyzing substrates (e.g., stains). These enzymes are known as hydrolases, which include, but are not limited to, proteases (bacterial, fungal, acid, neutral or alkaline), amylases (alpha or beta), lipases, cellulases, and mixtures thereof. Particularly preferred enzymes include those sold under the trade names Purafect, Purastar, Properase, Puradax, Clarase, Multifect, Maxacal, Maxapem, and Maxamyl by Genencor International (U.S. Pat. No. 4,760,025 and WO 91/06637); Alcalase, Savinase, Primase, Durazyme, Duramyl, and Termamyl sold by Novo Industries A/S (Denmark) Particularly preferred proteases are subtilisins. Cellulase is another preferred enzyme and particularly cellulases or cellulase components isolated from *Trichoderma reesei*, such as found in the product Clazinase. Preferred amylases include alpha amylases obtained from *Bacillus licheniformis*.

In one aspect, one or more active ingredients are incorporated in the core of the granule, in another preferred aspect one or more active ingredients are layered around the core, and in another aspect the active ingredients are in the flexible film coating. When layered around the core, the layer comprising the active ingredient may additionally include a binder such as a polymer as mentioned herein, preferably a vinyl polymer such as PVA.

The layer comprising the active ingredient layer may further comprise plasticizers and anti-agglomeration agents. Suitable nonlimiting examples of plasticizers useful in the present invention include polyols such as sugars, sugar alcohols or polyethylene glycols (PEGs) having a molecular weight less than 1000, ureas or other known plasticizers, such as dibutyl or dimethyl phthalate, or water. Suitable anti-agglomeration agents include fine insoluble material such as talc, $TiO_2$, clays and amorphous silica.

The granules of the invention may include between 0.01 to 50% by weight active ingredient. Particularly preferred are enzymes comprising at least 0.5%, at least 5%, at least 10%, at least 20%, at least 30% and up to and including 40%. The layer comprising the active ingredient, including any nonenzyme solids and binders therein, may comprise between about 0.01 to 50%, about 0.05 to 35%, about 0.1 to 15% and about 0.5 to 8.0% by weight of the granule.

Flexible Film

The term "flexible film" as used herein refers to a coating formed from a water-soluble or water dispersible polymeric material having an elongation upon break value of greater than about 30%; greater than 50%, greater than 100%, greater than 125%, greater than 150%, and greater than 200%. The percent elongation upon break is the most significant property defining the flexible film according to the invention. Elongation upon break may be measured by use of a stress/strain device such as manufactured by Instron (Canton Mass.).

For the purpose of the present invention, elongation upon break of a flexible film is measured on a test film. The test film is produced in the same manner as the film of the granule. This includes not only maintaining the film composition but also process conditions such as casting of the film as opposed to atomization. In one embodiment, an Instron stress/strain test is used to determine the elongation of a film. In this test, a test film is held in place between two jaws under pneumatic pressure. A constant strain rate is applied to the film while the stress on the film is measured and recorded by a load cell. American Society for Testing and Materials (ASTM) methods known to those in the art teach how to make these measurements. To use this device, a film of uniform thickness is prepared by the method of casting, for example by spin coating, a polymer solution onto a plate such as a stainless steel or glass plate followed by drying and removing the film from the plate. The test film can also be prepared by the method of spray-coating, for example by atomizing a polymer solution onto a plate such as stainless steel or glass plate followed by drying and removal of the film. The film is cut into samples, for example, into samples of approximately 25 mm in width and 70 mm in length. The film thickness may then be measured using a digital coating thickness gauge and is an average of a number of measurements along the length of the film.

While one skilled in the art is aware of water-soluble polymers and water dispersible polymers, in general a water-soluble polymer will have a solubility of at least 1%, preferably at least 5%, and frequently at least 15% in deionized water at room temperature. Water dispersible polymers are those which break up into fine particles of no greater than about 50 microns at room temperature within about 10 minutes of moderate agitation in deionized water or a solution of less than about 5% of a detergent or nonionic surfactant. Moderate agitation may be achieved for example by use of a stir bar at 200 rpm in a 200 ml beaker filled to 100 ml with aqueous solvent.

Preferred nonlimiting polymers are selected from polyvinyl alcohols (PVA), polyethylene glycols (PEG), polyethylene oxides (PEO), polyvinyl pyrrolidones (PVP), cellulose ethers, alginates, gelatin, modified starches and substituted derivatives, hydrolysates and copolymers thereof. Most preferred polymers are PVA, cellulose ethers, such as methyl cellulose and hydroxylpropyl cellulose, gelatin and modified starches, such as hyproxypropyl starch produced from cornstarch. Mostly preferred is PVA, however, it is not intended that the present invention be limited to any particular polymer. The polymers may be utilized in a foamed morphology. If PVA is used, in preferred embodiment the polymer has a level of hydrolysis in the range of about 50 to 99%, at least about 80%, at least about 85%, at least about 90%, and at least about 95%. The polymer may have an average molecular weight of about 4,000 to 250,000, preferably from 5,000 to 200,000; also from 10,000 to 100,000. For the purpose of the invention, a polymer comprising the flexible film may have a suitable viscosity below about 2000 cps, below 1000 cps and even below 500 cps at a temperature range of about 25 to 90° C. For the casting process step herein the viscosity is preferably 2000 cps or lower.

Suitable polymers also include natural and synthetic gelling agents. Nonlimiting examples include hydrocolloids or gums, such as gelatin, pectin, carrageenan, xanthan gum, gum arabic, alginate, agarose, or any combination thereof. These gelling agents may also be combined with the polymers as listed above. A gelling agent may comprise about 1 to 10%, about 2 to 8%, or about 4 to 6% of the flexible film. A preferred gelling agent comprising the flexible film is carrageenan. In one embodiment PVA and carrageenan comprise the flexible film.

Further, cross linking agents may be added to gel or modify the properties of the film and reduce or delay its solubility, for example boric acid may be used to cross link PVA and calcium salts may be used to cross link sodium alginate.

In a further embodiment, the polymer may be mixed with a plasticizer to form the flexible film according to the invention. Suitable plasticizers are nonvolatile solvents which may increase elongation upon break and thereby reducing the brittleness and enhancing deformability of the film. Typically plasticizers are low molecular weight organic compounds generally with molecular weights below 1000. Examples include, but are not limited to, polyols (polyhydric alcohols), for example alcohols with many hydroxyl groups such as glycerol, glycerin, ethylene glycol, propylene glycol, dipropylene glycol, polyethylene glycol, polar low molecular weight organic compounds, such as urea, sugars, sugar alcohols, oxa diacids, diglycolic acids, and other linear carboxylic acids with at least one ether group, dibutyl or dimethyl phthalate, or water. Sugars may include but are not limited to sucrose, dextrose, fructose, maltose, trehalose, and raffinose. Sugar alcohols that may serve as plasticizers include sorbitol, xylitol, and maltitol. Also included are wax, ethanolacetamide, ethanolformamide, triethanolamine acetate, sodium thiocyanates, and ammonium thiocyanates. Most preferred are glycerol, propylene glycol, sorbitol, and polyethylene glycol having an average molecular weight below about 600. The plasticizer is preferably present at a level of 1 to 75% by weight of the polymer, preferably about 5 to 50% by weight of the polymer. The exact level will depend on the polymeric material and plasticizer comprising the film. For example when glycerol is used as a plasticizer for a gelatin film, the level is preferably about 20 to 50% by weight of the polymer.

The flexible film comprises preferably less than about 20% by weight of the granule. In further embodiments, the flexible film comprises preferably less than about 15%, less than about 10%, less than about 8%, and about 5% to 20% by weight of the granule.

The flexible film may also include further components such as, but not limited to fillers, lubricants, and pigments. These compounds are well known to one of ordinary skill in the art and are further discussed herein.

In one embodiment the invention concerns converting an impact-sensitive particle to a highly impact-resistant granule. This is achieved by applying a flexible film according to the invention to an impact-sensitive particle. One skilled in the art can determine an impact-sensitive particle by standard tests known in the art and as described herein. In one preferred embodiment, an impact-sensitive particle will have a mass attrition of at least 20% when measured at 216,000 collisions by RIT. In another embodiment an impact-sensitive particle will have a mass attrition of at least 50% when measured at 216,000 collisions by RIT. In this regard the impact sensitive particle may be a particle or granule made by extrusion (U.S. Pat. No. 5,739,091), prilling, drum granulation (WO 9009440) and various other well-known methods. Then using the casting process as taught herein an impact sensitive particle may be converted to a highly impact-resistant granule of the invention.

One specific non-limiting example includes the T-granulation process of Novo-Nordisk which provides for the inclusion within a composition undergoing granulation, of finely divided cellulose fibers, salts and binders added to enzymes and formed into granules using high shear granulators or drum granulators. In addition a waxy substance can be used to coat the granules and further coating layers may be applied (See U.S. Pat. No. 4,106,991). Even though the obtained granule is tough and somewhat resistant to compression, it is not very resistant to repeated impact forces (See U.S. Pat. No. 5,324,649) and is considered an impact-sensitive particle according to the definition herein. A flexible film according to the invention applied to the T-granule may convert the T-granule from an impact-sensitive particle to a highly impact-resistant granule according to the present invention.

Other Layers

The granules of the present invention which include the flexible film coating may further comprise one or more other coating layers. For example, such coating layers may be one or more intermediate coating layers defined as a coating layer under the flexible film. Additionally, one or more coating layers may be one or more over-coating layers, wherein a coating is applied over the flexible film. A combination of one or more intermediate coating layers and one or more over-coating layers may also comprise the granules. Coating layers may serve any of a number of functions depending on the end use of the granule. For example, coatings may render the active ingredient, particularly enzymes, resistant to oxidation by bleach, or coating layers may bring about the desirable rate of dissolution upon introduction of the granule into an aqueous medium, or provide a further barrier against ambient moisture in order to enhance the storage stability of the granule and reduce the possibility of microbial growth within the granule.

In an embodiment of the present invention, the coating layer comprises one or more polymer(s) and, optionally, a low residue pigment or other excipients such as lubricants. Such excipients are known to those skilled in the art. Furthermore, coating agents may be used in conjunction with other active agents of the same or different categories.

Suitable polymers include PVA and/or PVP or mixtures of both. If PVA is used, it may be partially hydrolyzed, fully hydrolyzed or intermediately hydrolyzed PVA having low to high degrees of viscosity (preferably partially hydrolyzed PVA having low viscosity). Other vinyl polymers which may be useful include polyvinyl acetate and polyvinyl pyrrolidone. Useful copolymers include, for example, PVA-methylmethacrylate copolymer. Other polymers such as PEG may also be used in the outer layer. These further coating layers may further comprise one or more of the following: plasticizers, pigments, lubricants such as surfactants or antistatic agents and, optionally, additional enzymes. Suitable plasticizers useful in the coating layers of the present invention are those disclosed herein above. Suitable pigments useful in the coating layers of the present invention include, but are not limited to, finely divided whiteners such as titanium dioxide or calcium carbonate, or colored pigments, or a combination thereof. Preferably such pigments are low residue pigments upon dissolution.

As used herein "lubricants" mean any agent which reduces surface friction, lubricates the surface of the granule, decreases static electricity or reduces friability of the granules. Lubricants can also play a related role in improving the coating process, by reducing the tackiness of binders in the coating. Thus, lubricants can serve as anti-agglomeration agents and wetting agents.

Suitable lubricating agents include, but are not limited to, surfactants (ionic, nonionic or anionic), fatty acids, antistatic agents and antidust agents. Preferably the lubricant is a surfactant, and most preferably is an alcohol-based surfactant such as a linear, primary alcohol of a 9 to 15 carbon atom chain length alkane or alkene or an ethoxylate or ethoxysulfate derivative thereof. Such surfactants are commercially available as the Neodol® product line from Shell International Petroleum Company. Other suitable lubricants include, but are not limited to, antistatic agents such as StaticGuard™, Downey™, Triton X100 or 120 and the like, antidust agents such as Teflon™ and the like, or other lubricants known to those skilled in the art.

Other intermediate layers, such as binders, structuring agents, and barrier layers may be included. Suitable barrier materials include, for example, inorganic salts, sugars, or organic acids or salts. Structuring agents can be polysaccharides or polypeptides. Preferred structuring agents include starch, modified starch, carrageenan, cellulose, modified cellulose, gum arabic, guar gum, acacia gum, xanthan gum, locust bean gum, chitosan, gelatin, collagen, casein, polyaspartic acid and polyglutamic acid. Preferably, the structuring agent has low allergenicity. A combination of two or more structuring agents can be used in the granules of the present invention. Binders include but are not limited to sugars and sugar alcohols. Suitable sugars include but are not limited to sucrose, glucose, fructose, raffinose, trehalose, lactose and maltose. Suitable sugar alcohols include sorbitol, mannitol and inositol.

The other non-film coating layers of the present invention preferably comprise between about 1–20% by weight of the granule including the flexible film coating.

Other Adjunct Ingredients

Adjunct ingredients may be added to the granules of the present invention, including but not limited to: metallic salts, solubilizers, activators, antioxidants, dyes, inhibitors, binders, fragrances, enzyme protecting agents/scavengers such as ammonium sulfate, ammonium citrate, urea, guanidine hydrochloride, guanidine carbonate, guanidine sulfonate, thiourea dioxide, monethyanolamine, diethanolamine, triethanolamine, amino acids such as glycine, sodium glutamate and the like, proteins such as bovine serum albumin, casein and the like, etc., surfactants, including anionic surfactants, ampholytic surfactants, nonionic surfactants, cationic surfactants and long-chain fatty acid salts, builders, alkalis or inorganic electrolytes, bleaching agents, bluing agents and fluorescent dyes, and caking inhibitors. These surfactants are described in PCT Application PCT/US92/00384, which is incorporated herein by reference.

Processes for Making the Granule with Flexible Film

In general, methods well known in the art of enzyme granulation, including fluidized bed-spray-coating, pan-coating and other techniques may be used for making part of the granule according to the invention, including the core, active ingredient layer and optionally intermediate or over-coating layers. However, surprisingly it has been found that the means of applying the flexible film coating may be a critical step in providing a granule according to the invention herein having improved characteristics such as highly impact-resistant, ultra low dust and increased stability.

A preferred process for applying the flexible film herein comprises obtaining a polymer and then casting the polymer generally in liquid or molten form on to the core or an active ingredient layer. Casting is a process well known in the confectionary industry used to make desserts such as gelatin or candies such as gumdrops. In the present invention casting is used not to make particles but to apply film coatings to particles.

According to the present invention, casting is a process in which a particle including a core and one or more active ingredients is enveloped within a continuous film of liquid or molten material and which is rapidly solidified, from about 1 second to about 2 minutes, by cooling, hardening, gelation, crosslinking or other such means of converting a liquid film into a solid film. Gelation is preferably thermal gelation.

Figure 2:
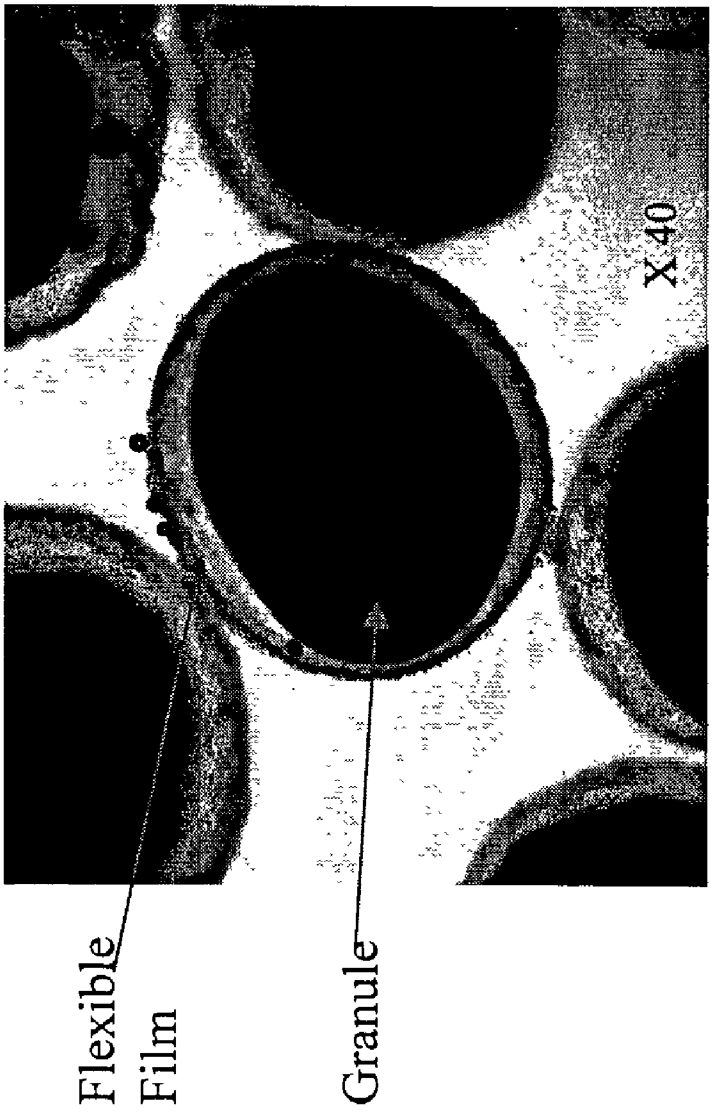
FIG. 2 is a 40× magnification cross-section view of a granule having a flexible film of the present invention.

The thickness of the film is determined by the specific process of removing excess film liquid, for example by drainage or centrifugal force. The formulations and processes of the present invention allow for thin films generally of a thickness of less than 20 μm, and preferably less than 15 μm. Typical coatings used in the Examples were as thin as approximately 10 μm , and may of course be thicker if desired. The small amount of flexible coating relative to the rest of the granule is illustrated in FIG. 2.

A casting process is further distinguished from an atomization or layering process because a cast film is homogenous at a microscopic level and is not built up from deposition of discretely atomized droplets or patches, as shown in FIG. 1. In FIG. 1, the spray-coated film on the right contains multi-layers and was atomized into fine droplets using a nozzle and sprayed uniformly onto a plate. The spin-coated film on the left forms a uniform coherent film without layers.

The film should remain stable and continuous and not be so soft or tacky so as to render the granule unhandleable. A stable granule is one wherein the film is attached to the core and active ingredient layer and the granule is free flowing, easy to handle and not tacky. Casting may be applied by a number of techniques referred to as dipping, spinning disk, and emulsion gelation and reference is made to U.S. Pat. No. 4,675,140; U.S. Pat. No. 4,123,206; U.S. Pat. No. 3,423,489; and Kirk-Othmer Encyclopedia of Chemical Technology, 3rd ed., vol. 15, pp 470–492 (1981) and particularly pages 473–474 as it relates to casting. According to the present invention casting is preferably applied by spinning disk (see U.S. Pat. No. 4,675,140 and Goodwin et al., (1974) Chem Tech 4:623 in Vandegaer, ed., Microencapsulation: Process and Applications, Plenum Press, NY pgs. 155–163) wherein a suspension of the film coating solution or molten liquid and core material including the active ingredient are centrifugally thrown from the disk surface and formed into discrete coated particles, following by solidification of the film. The resulting granules are collected in a powder bed, or non-solvent cooling bath or cooling chamber. The resulting granule will be a highly impact-resistant granule having a mass attrition of about less than 10%.

In a preferred embodiment, a gelling agent is included with the flexible film. In another preferred embodiment the flexible film includes the polymer, gelling agent and a plasticizer (particularly preferred are PVA, the gelling agent carrageenan and a glycerol plasticizer). The polymer and gelling agent may be dissolved into a plasticizer water mixture at a temperature above the gel point of the gelling agent. Upon dissolution of the polymer and gelling agent, the core particles, either including an active ingredient in the core or surrounding the core, are combined with the coating solution or molten liquid. The suspension may then be poured onto a rotating surface. Granules comprising the flexible film are collected and allowed to dry.

In one embodiment, one or more active ingredients will be incorporated into the core and in another embodiment one or more active ingredients will comprise a layer surrounding the core.

In another preferred process, the highly impact-resistant granule is produced by combining a polymer and a plasticizer to obtain a water-soluble or water dispersible mixture; obtaining a core material comprising an active ingredient; and casting said mixture onto the core, wherein said flexible film includes PVA and glycerol and carrageenan.

While casting has been described as the preferred method for applying the flexible film coating of the present invention, it will be understood by those skilled in the art that the invention includes any coating method that results in the application of a flexible film coating as defined herein, namely a coating having an elongation upon break of at least about 30%, and less than about 10% RIT mass attrition.

Compositions Comprising the Highly Impact-Resistant Granule

The granules according to the invention may be incorporated in any number of compositions which require active ingredients to be protected against inactivation by elevated temperature, humidity or exposure to denaturants, oxidants or other harsh chemical and physical forces. In particular, the granules are useful in cleaning compositions, fabric care compositions, personal care compositions and pharmaceutical compositions. Preferred compositions include detergent compositions including laundry and dishwashing compositions. The compositions typically include one or more compounds particularly surfactants (See WO 9206165). Pharmaceutical compositions and personal care compositions including one or more additives are also preferred.

EXPERIMENTAL

Example 1

Impact-Sensitive Particle Including a Core and Active Ingredient

Core particles were prepared by charging sucrose crystals into a fluidized bed coater and spraying a solution of 41.8% sucrose and 20.9% suspended starch on the crystals such that the sucrose crystals constitute 28% of the built-up cores. An overcoat layer of 2.3% PVA (Moviol 3-83, Clariant, Charlotte, N.C.) and 7% corn starch was added on the basis of the core weight. A solution of ultrafiltration concentrate containing 80–90 g/L of subtilisin protease sufficient to deliver 8% w/w subtilisin to the final granule was sprayed onto the particles. Then a solution of methylcellulose (Dow Methocel A-15), polyethylene glycol of molecular weight 600, and titanium dioxide was sprayed on top of the granule so as to deposit a film coating of 5% methylcellulose, 1.6% PEG 600 and 6.2% titanium dioxide on a w/w basis and 1% w/w Neodol 23-6.5T Shell Chemical nonionic surfactant. Also a further overcoating of 0.75% w/w Neodol 23-6.5T was applied.

The granules were tested in the RIT. About 30 mg of granules were placed into an aluminum box of dimensions 2 cm×3 cm×1.5 cm and oscillated up and down at a frequency of 60 Hz causing the granules to impact the walls of the box at an impact velocity of 8.52 meters/second. The box was sealed to completely contain all of the dust generated during the test procedure. The test was run during 30 minutes resulting in 216,000 impacts or collisions with the box walls. At various time intervals (60 seconds, 120 seconds, see table 1 below), the box was opened and the content of the box was sieved through a 300 μm sieve to remove any fines or damaged particles. The percent mass attrition was determined and the undamaged fraction was put back into the box for further testing. The results of percent mass attrition are reported in Table 1 which shows 61.56% mass attrition after 216,000 collisions. Under the enzyme dust test conditions 2,805,588 ng/g RIT enzyme dust was produced.

TABLE 1

| | | Impact-sensitive particles without flexible film | |
|---|---|---|---|
| Time (s) | Collisions N | m = mass retained (g) | % mass attrition |
| 0 | 0 | 0.0333 | 0.00% |
| 60 | 7200 | 0.0332 | 0.30% |
| 120 | 14400 | 0.0328 | 1.50% |
| 240 | 28800 | 0.0299 | 10.21% |
| 420 | 50400 | 0.0261 | 21.62% |
| 600 | 72000 | 0.0228 | 31.53% |
| 900 | 108000 | 0.0194 | 41.74% |
| 1200 | 144000 | 0.0165 | 50.45% |
| 1800 | 216000 | 0.0128 | 61.56% |

Example 2

RIT Testing of Another Impact-Sensitive Particle Containing an Active Ingredient Commercially available samples of enzyme granules produced by the T-granulation process as disclosed in U.S. Pat. No. 4,106,991 and U.S. Pat. No. 4,876,198 and developed by Novo-Nordisk were evaluated in the RIT for mass attrition. Two granules were tested, Savinase 6.0T and Savinase 12 TXT. The tests below in Table 2 indicated that the T-granules are impact-sensitive.

TABLE 2

| | | Savinase 6.0T | | Savinase 12 TXT | |
|---|---|---|---|---|---|
| Time (s) | Collisions N | m = mass retained (g) | % mass Retained | m = mass retained (g) | % mass Retained |
| 0 | 0 | 0.0366 | 100% | 0.0308 | 100% |
| 60 | 7200 | 0.0296 | 80.87% | 0.0248 | 80.52% |
| 120 | 14400 | 0.0238 | 65.03% | 0.0198 | 64.29% |
| 240 | 28800 | 0.0183 | 50.00% | 0.0148 | 48.05% |
| 420 | 50400 | 0.0125 | 34.15% | 0.0109 | 35.39% |
| 600 | 72000 | 0.0094 | 25.68% | 0.0082 | 26.62% |
| 900 | 108000 | 0.0061 | 16.67% | 0.0041 | 13.31% |
| 1200 | 144000 | 0.0037 | 10.11% | 0.002 | 6.49% |
| 1800 | 216000 | 0.0013 | 3.55% | 0.0007 | 2.27% |

Example 3

Spinning Disk Casting Process for Preparing Impact Resistant Granules with Flexible Films A film coating solution comprising 20 g PVA (Mowiol 3-83 from Clariant, Charlotte, N.C.), 20 g glycerol (from J T Baker), 1 g carrageean (Gelcarin GP-911 from FMC Corp., Philadelphia, Pa.), 6.1 g Titanium Dioxide and 46 g water was prepared by dissolving PVA and carrageenan into the glycerol and water mixture and bringing the temperature to 95° C. Temperature was maintained at 95° C. until complete dissolution of the PVA and carrageenan. Titanium dioxide was then introduced into the film coating solution.

46 g of impact sensitive granules as described in Example 1 were added into 200 ml of film coating solution at a temperature of 90° C. The slurry was mixed for 5 seconds using a marine impeller and poured onto a 4 inch spinning disk rotating at a speed of 3000 rpm at an approximate rate of 1 L/min. The granules comprising the IS flexible film were collected from the rotating device onto a bed of corn starch (DryFlow from National Starch) at ambient temperature. The collected granules were allowed to air dry overnight.

Table 3 illustrates the compositions of 4 additional PVA flexible film coatings applied to the impact sensitive granules of Example 1 by the spinning disk process. Table 4 illustrates the compositions of five gelatin flexible films that were applied to the impact sensitive granules of Example 1 by the spinning disk process. Table 5 illustrates the composition of a modified starch flexible film that was applied to the impact sensitive granules of Example 1 by the spinning disk process.

TABLE 3

Composition of granule with PVA/carrageenan flexible film.

| Ingredients | Sample 1 wt (g) | 2 | 3 | 4 | 5 |
|---|---|---|---|---|---|
| Mowiol 3-83 | 20 | 20 | 20 | 20 | 20 |
| Glycerol | 0 | 3 | 6 | 10 | 20 |
| TiO2 | 3.2 | 3.6 | 4 | 4.6 | 6.1 |
| Carrageenan | 1 | 1 | 1 | 1 | 1 |
| Water | 78.9 | 72.4 | 69 | 64.4 | 52.9 |
| Core granules | 24 | 27 | 30 | 34.5 | 46 |

TABLE 4

Composition of granule with gelatin flexible film.

| Ingredients | Sample 6 wt (g) | 7 | 8 | 9 | 10 |
|---|---|---|---|---|---|
| Gelatin Type A Bloom 150 (Leiner-Davis, Jericho, NY) | 25 | 25 | 25 | 25 | 25 |
| Glycerol | 0 | 3.8 | 7.5 | 12.5 | 25 |
| Water | 75 | 71.3 | 67.5 | 62.5 | 50 |
| Core granule | 25 | 28.8 | 32.5 | 37.5 | 50 |

TABLE 5

Composition of granules with modified starch/carrageenan flexible film.

| Ingredients | Sample 11 wt (g) |
|---|---|
| Pure-Cote B790 (GPC Muscatine, IA) | 25 |
| Glycerol | 25 |
| Carrageenan | 1 |
| Water | 49 |
| Core granule | 50 |

Example 4

Emulsion Gelation Casting Process for Preparing Impact Resistant Granules with a Flexible Film A film solution composed of 28 g Pork skin gelatin Type A Bloom 275, 12 g glycerol and 60 g water was first prepared by premixing glycerol and water, adding gelatin to the water/glycerol mixture and bring the temperature to 80° C. The temperature and agitation were maintained until complete dissolution of the gelatin.

0.2 g of core granules made according to Example 1 were added into 20 ml of the coating solution at 55° C. and mixed with a spatula for 5 seconds. The slurry comprising the granules and gelatin film coating was immediately poured into 100 ml of corn oil containing 1 w/w % Span 80 at a temperature of 55° C. and emulsified under low agitation using a marin impeller at 100 rpm. Agitation was increased to 300 rpm and maintained for 3 minutes. After 3 minutes, 100 ml of corn oil pre-cooled at 0° C. was introduced to the reactor and agitation was reduced to 150 rpm including gelation of the film coating on the core granules. After 5 minutes, the dispersion of gelatin coated granules was poured into 200 ml of cold acetone. The coated granules were filtered, rinsed four times using 200 acetone containing 1% between 80, and then air-dried.

Example 5

Film Properties of Impact Resistant Granules Formed by the Spinning Disk Process A number of the granules having coatings applied using the spinning disk process (Example 3) were tested to determine the properties set out below.

1. Process described in Example 3—Gelatin cast film/spinning disk granules.

| Sample | Film and granule coating Composition % Gelatin | % Glycerol | Film Tensile Strength (M Pa) | Film Modulus (M Pa) | Film Elongation (%) | Granule RIT Enzyme Dust (ng/g) |
|---|---|---|---|---|---|---|
| 6 | 100 | 0 | 68 | 2426 | 3.2 | 1,245,000 |
| 7 | 87 | 13 | 30 | 971 | 13 | 360,800 |
| 8 | 77 | 23 | 2.7 | 3.3 | 178 | 83,540 |
| 9 | 67 | 33 | 1.5 | 1.2 | 150 | 38,500 |
| 10 | 50 | 50 | | | | 2,522 |

2. Process described in Example 3—PVA & Carrageenan cast films/Spinning disk granules.

| | Film and granule coating Composition | | Film Tensile Strength | Film Modulus | Film Elongation | Granule RIT Enzyme Dust |
|---|---|---|---|---|---|---|
| Sample | % PVA | % Glycerol | (M Pa) | (M Pa) | (%) | (ng/g) |
| 1 | 100 | 0 | 20.5 | 115 | 74 | 2,338 |
| 2 | 87 | 13 | 7.1 | 46 | 43 | 2,811 |
| 3 | 77 | 23 | 3.8 | 21 | 39 | 1,787 |
| 4 | 67 | 33 | 2.7 | 14 | 36 | 1,090 |
| 5 | 50 | 50 | | | | 2,006 |

3. Process described in Example 3—Modified starch and Carrageenan cast films/Spinning disk granules.

| | Film and granule coating Composition | | Film Tensile Strength | Film | Film Elongation | Granule RIT Enzyme Dust |
|---|---|---|---|---|---|---|
| Sample | % modified starch | % Glycerol | (M Pa) | (M Pa) | (%) | (ng/g) |
| 11 | 50 | 50 | | | | 7,676 |

In addition to the properties given above for flexible films applied by a spinning disk process, the granules made by the emulsion gelation process of Example 4 were tested to determine impact resistance using the Repeated Impact Machine described in U.S. Pat. No. 6,035,716. They were compared to reinforced nonpareil cores composed of starch and sucrose prepared by the process described in Example 1. The following procedure was used in obtaining these results as shown in Table 6. About 30 mg of granules with the emulsion gelation applied flexible film coating were placed into an aluminum box of dimensions 2 cm×3 cm×1.5 cm and and down at a frequency of 60 Hz causing the granules to impact the walls of the box at an impact velocity of 8.52 meters/second. The box was sealed to completely contain all of the dust generated during the test procedure. The test was run during 30 minutes (216,000 impacts or collisions with the box walls). At various time intervals (60 seconds, 120 seconds, see table 5 below), the box was opened and the content of the box was sieved through a 300 μm sieve to remove any fines or damaged particles. The percent mass attrition was determined and the undamaged fraction was put back into the box for further testing

TABLE 6

| | | Granules with Gelatin Film Applied by Emulsion Gelation | |
|---|---|---|---|
| Time (s) | Collisions N | m = mass retained (g) | % mass Attrition |
| 0 | 0 | 0.032 | 0.00% |
| 60 | 7200 | 0.0315 | 1.56% |
| 120 | 14400 | 0.0315 | 1.56% |
| 240 | 28800 | 0.0313 | 2.19% |
| 420 | 50400 | 0.0314 | 1.88% |
| 600 | 72000 | 0.0315 | 1.56% |
| 900 | 108000 | 0.0316 | 1.25% |

TABLE 6-continued

| | | Granules with Gelatin Film Applied by Emulsion Gelation | |
|---|---|---|---|
| Time (s) | Collisions N | m = mass retained (g) | % mass Attrition |
| 1200 | 144000 | 0.0316 | 1.25% |
| 1800 | 216000 | 0.0316 | 1.25% |

The spinning disk process results indicate that the process produces PVA, gelatin, and modified starch flexible films with acceptable RIT dust values. The results also demonstrate that flexible films added by spinning disk are in general elastic. These results are illustrated in the film elongation and RIT dust results for nine of the tested granules which may be classified as highly impact resistant granules as defined herein.

The results shown in Table 6 illustrate that flexible film coatings applied using an emulsion gelation casting process also are impact resistant as shown by the low mass attrition values.

Gelatin based films (Sample 10 above) applied by the spinning disk process also were tested to determine mass retention values as shown below in Table 7. The Table 7 results illustrate acceptable mass retention values for impact resistant granules as opposed to the control granule (Example 1) without the flexible gelatin coating.

TABLE 7

| Time (s) | N | Control Granule | Granule with Gelatin Film |
|---|---|---|---|
| 0 | 0 | 100.00% | 100.00% |
| 60 | 7200 | 99.12% | 98.40% |
| 120 | 14400 | 93.86% | 98.72% |

TABLE 7-continued

| Time (s) | N | Control Granule | Granule with Gelatin Film |
|---|---|---|---|
| 240 | 28800 | 80.70% | 98.40% |
| 420 | 50400 | 68.42% | 98.40% |
| 600 | 72000 | 60.53% | 98.40% |
| 900 | 108000 | 51.75% | 98.40% |
| 1200 | 144000 | 47.37% | 97.76% |
| 1800 | 216000 | 40.06% | 97.76% |

Figure 3:
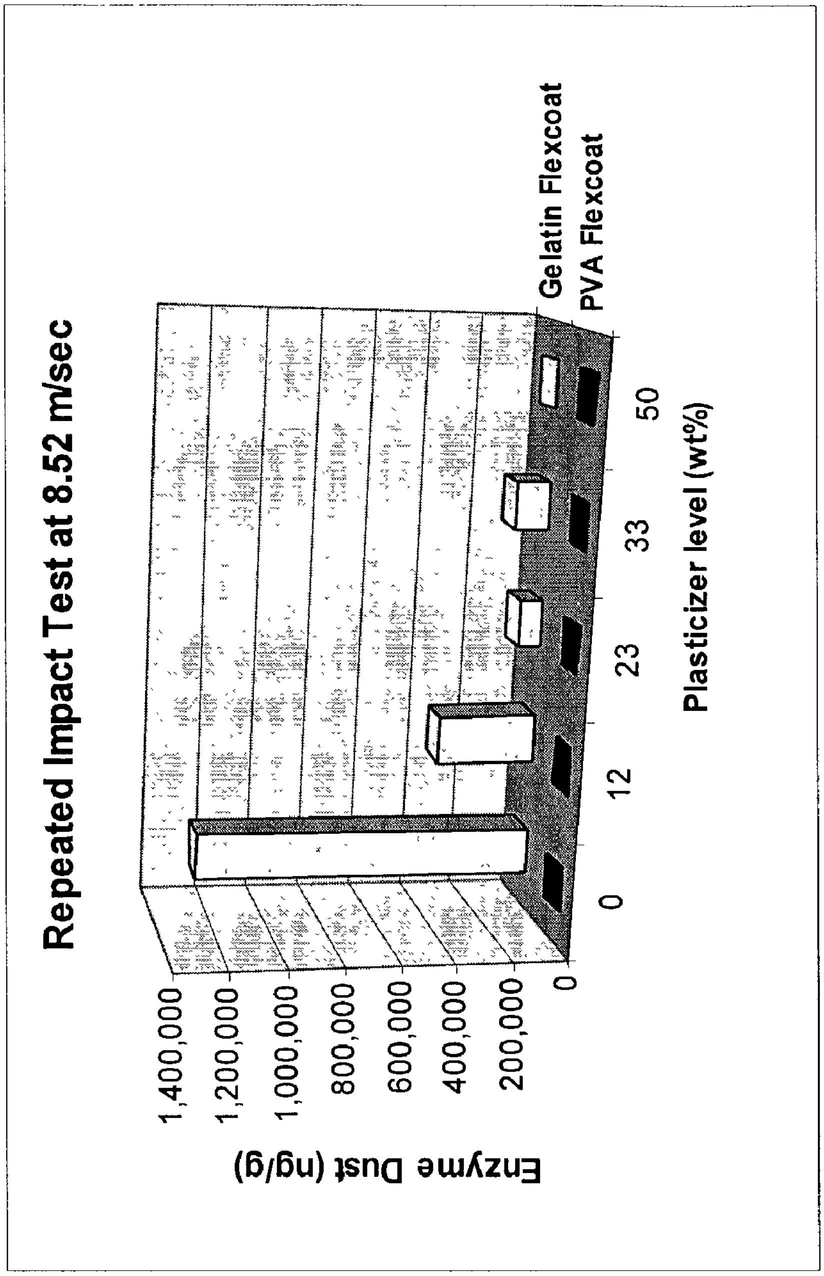
FIG. 3 is a graph showing acceptable enzyme dust figures for PVA polymer flexible films with and without the addition of a plasticizer.

The effect of varying levels of plasticizer for the various granules prepared by the spinning disk process is best shown in FIG. 3. FIG. 3 illustrates graphically that the PVA flexible films all exhibit low enzyme dust values with and without different levels of plasticizer, while gelatin based flexible films exhibit higher dust values without plasticizer.

Example 7

Spray Coating Process for Preparing Granules Having a Flexible Coating

Tests were performed to determine whether the PVA based flexible film coatings of the present invention could be applied using a spray coating procedure to produce impact resistant granules.

Granules were prepared in a Vector FL-1 fluid-bed coater. The composition of the cores of the granules is similar to the core composition in Example 1. Reinforced cores were first prepared by spraying an aqueous mixture of starch and sucrose onto sucrose crystals, then these particles were coated with a PVA/starch coating such that the reinforced nonpareils contain 38.0% sucrose crystals, 52.7% of 2:1 sucrose/starch mixture, and 9:3% of a 3:1 starch/PVA mixtures. The reinforced cores were then sequentially coated with enzyme and polymer layers. 639 g of reinforced cores prepared by this method were charged in a Vector FL-1 coater and fluidized temperature of 65° C. 714 g of protease ultra filtration concentrate containing 58 g/kg protease were sprayed on the reinforced non pareils under the following conditions:

Fluid feed rate: 20 grams/min
Atomization pressure: 40 psi
Inlet temperature: 85° C.
Outlet temperature: 60° C.
Fluidization air rate: 80 cfm Finally, the four film coating mixtures shown in Table 8 below, having polymer to plasticizer ratios similar to those shown for the spinning disk process PVA granules described in Example 3 were prepared by dispersing the polyvinyl alcohol (Clariant Mowiol 3-83) and glycerol (Samples 13, 14, and 15) into water. The temperature was brought to 95° C. and titanium dioxide was then introduced into the polymer solution. The coating mixtures were cooled to 50° C. before spraying over the enzyme-coated cores under the following conditions. The flexible film composition also was used to produce corresponding stand alone films for tensile strength measurements.

Fluid feed rate: 20 grams/min
Atomization pressure: 40 psi
Inlet temperature: 85° C.
Outlet temperature: 60° C.
Fluidization air rate: 80 cfm

TABLE 8

| | Sample | | | |
|---|---|---|---|---|
| | 12 | 13 | 14 | 15 |
| Ingredients | wt (g) | | | |
| Moviol 3-83 | 118 g | 106 g | 83 g | 74 g |
| Glycerol | 0 g | 17 g | 25 g | 37 g |
| TiO2 | 18 g | 19 g | 16 g | 17 g |
| Water | 684 g | 572 g | 423 g | 340 g |

The results are shown below in Table 9.

TABLE 9

PVA sprayed films/spray coated granules.

| | Film and granule coating Composition | | Film Tensile Strength | Film Modulus | Film Elongation | Granule RIT Enzyme Dust |
|---|---|---|---|---|---|---|
| Sample | % PVA | % Glycerol | (M Pa) | (M Pa) | (%) | (ng/g) |
| 12 | 100 | 0 | 3.1 | 112 | 16 | 2,935,788 |
| 13 | 87 | 13 | 0.5 | 8.1 | 15 | 1,267,195 |
| 14 | 77 | 23 | 3 | 17 | 39 | 2,333,191 |
| 15 | 67 | 33 | 1.7 | 9.9 | 35 | 176,049 |

Figure 5:
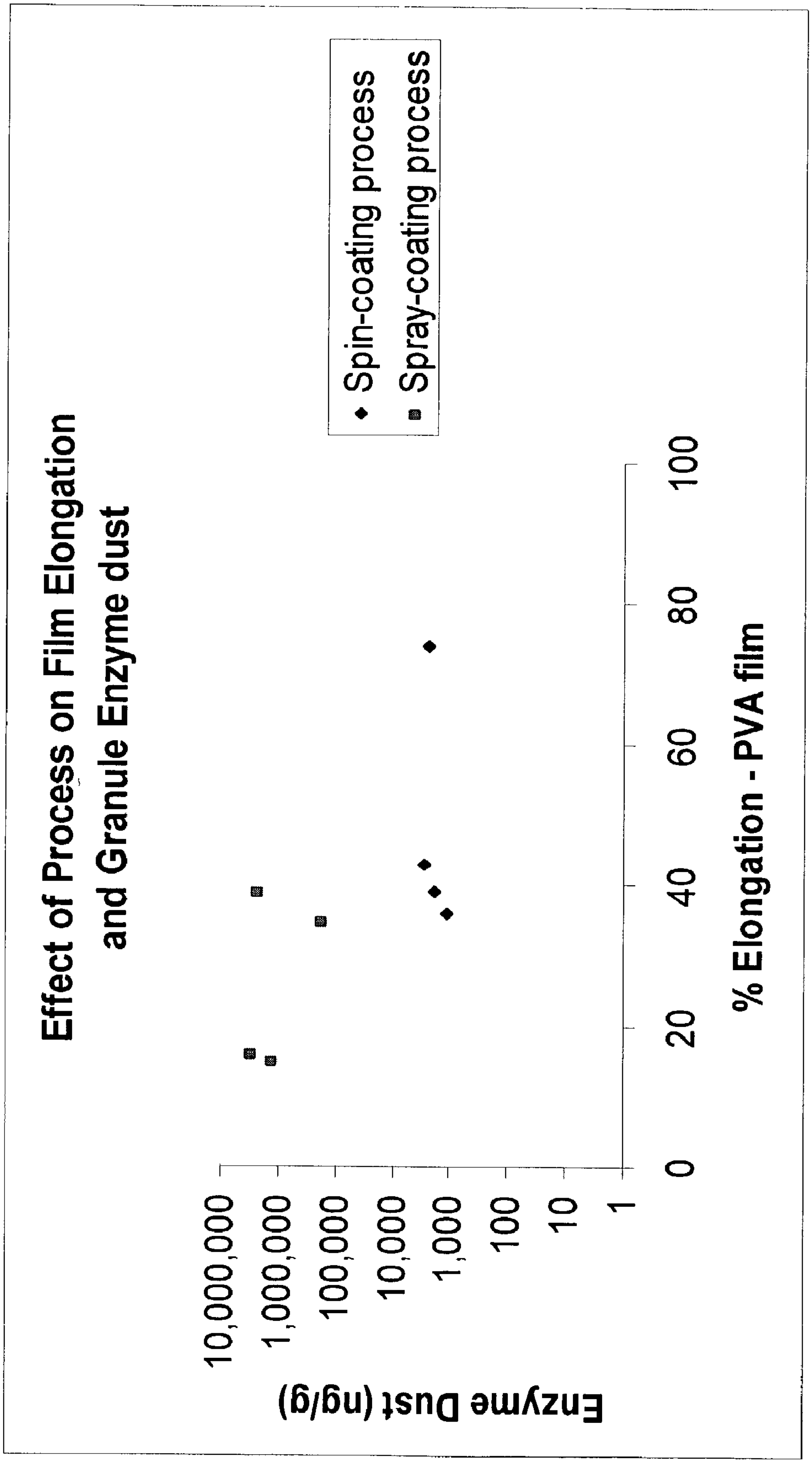
FIG. 5 is a graph showing elongation upon break and RIT enzyme dust values for spin-coated flexible film granules and for spray-coated flexible film granules.

Table 9 illustrates that one of the spray coated flexible films resulted in impact resistant granules having acceptable RIT enzyme dust values together with an acceptable film elongation value, namely, Sample 15, although the RIT dust value of Sample 15 was above the nreferred RIT dust value of less than about 100,000 ng/g. While impact resistant flexible films meeting the criteria as defined herein may be prepared by a spray coating process, the enzyme dust and film elongation values are superior for flexible film coatings prepared by casting, as best shown graphically in FIG. 5. FIG. 5 illustrates the dual advantages of the casting process, namely, the production of granules having both low dust values and increased elongation properties thereby reducing the effect of impact forces to maintain granule mass.

Example 7

Preparation and Testing of Flexible Core Granules

Instead of adding the flexible film material of the present invention as a coating, granules were prepared having a flexible gelatin core. The granules were prepared by adding 140 g of gelatin type A, Bloom strength 300, to 300 g of water at 80° C., under agitation until complete dissolution of the gelatin. 60 g of glycerin were added to the warm gelatin solution. The composition was then atomized into a 10° F. mixture of mineral oil and hexane at a 80:20 ratio using a 508 μm nozzle. The gelatin cores, formed with a size range of from 1000 to 1400 μm in diameter, were separated from the oil and transferred successively into two acetone baths at 10° F. and room temperature. The solidified cores were then separated from the acetone and allowed to dry at room temperature under a hood.

The gelatin cores were then sequentially coated with enzyme, salt and polymer layers in a fluid bed coater. 150 g of gelatin cores were charged into a Uniglatt fluidized bed coater with a Wurster insert, and fluidized to a bed temperature of 44° C. 235 g of protease ultrafiltration concentrate containing 61 g/kg subtilisin protease were sprayed onto the gelatin cores under the following conditions:

Fluid feed rate: 3.8–5.7 g/min
Atomization pressure: 35 psi
Inlet temperature: 50° C.
Outlet temperature: 40° C.
Fluidization air rate: 40% flap opening A solution of magnesium sulfate was prepared by adding 64 g of magnesium sulfate to 65 g water. The solution was then sprayed onto the enzyme coated gelatin cores under the following conditions Fluid feed rate: 4.6–6.3 g/min
Atomization pressure: 35 psi
Inlet temperature: 50° C.
Outlet temperature: 40° C.
Fluidization air rate: 40% flap opening Finally, a coating mixture was prepared by dispersing 18 g of polyvinyl alcohol (Dupont Elvanol 51-05) into 208 g water. The temperature was brought to 90° C. 23 g of titanium dioxide and 5 g nonionic surfactant (Shell Neodol 23-6.5T) nonionic surfactant were then introduced into the polymer solution. The coating mixture was cooled to 50° C. before spraying over the salt- and enzyme-coated gelatin cores under the following conditions.

Figure 4:
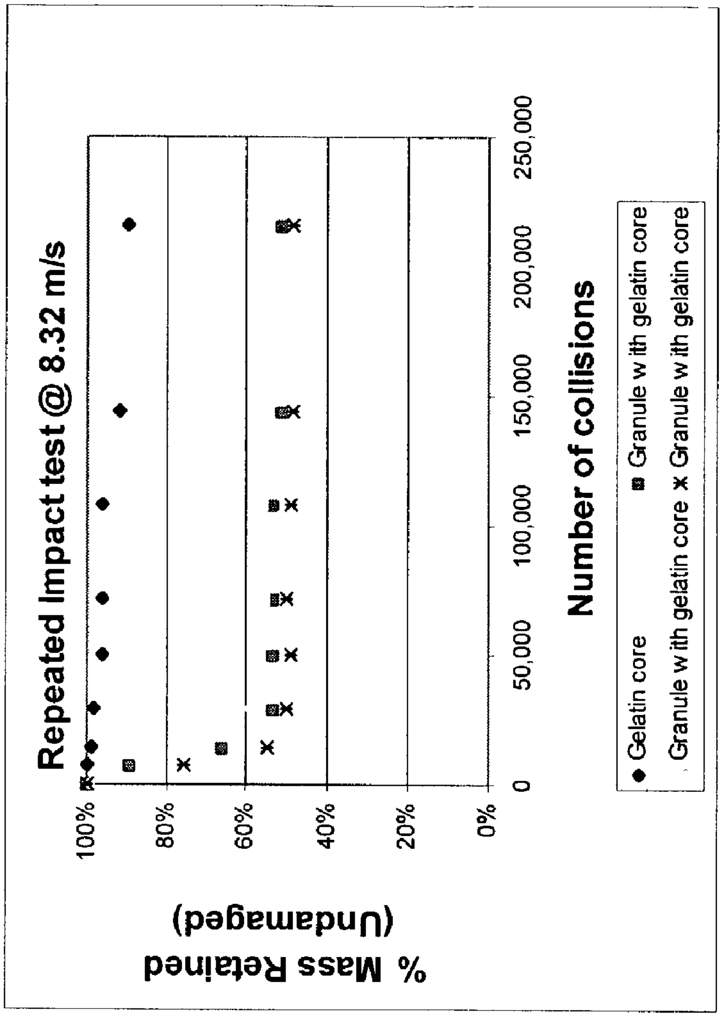
FIG. 4 is a graph showing unacceptable mass retention values for granules having a flexible core instead of a flexible film outer coating.

Fluid feed rate: 4.6–6.3 g/min
Atomization pressure: 35 psi
Inlet temperature: 50° C.
Outlet temperature: 40° C.
Fluidization air rate: 40% flap opening Utilizing a flexible material core did not produce impact resistant granules as illustrated by the RIT results shown in FIG. 4. FIG. 4 shows RIT mass retained results for a gelatin core control and three flexible core granules. The results demonstrate that the coating layers of the granule were rapidly lost prior to 50,000 collisions and then the weight loss remained constant for the remaining flexible gelatin core. The adhesion of the coated layer on the flexible core was found to be inferior to the adhesion of coated layers on the sucrose cores prepared by casting and spray coating processes. Without intending to be bound by any particular theory, it is believed that coating layers are unable to attach securely to the flexible core material and delaminate when subjected to impact forces.

Example 8

Enzyme Stability

As expected, the flexible impact resistant films of the present invention do not compromise enzyme stability during storage of the granules. Enzyme granules with the flexible film of the present invention exhibited storage stability that is comparable to storage stability exhibited by granules without the flexible film. For example, protease granules with and without flexible gelatin film coatings were tested after high stress storage in detergent for three days at 50° C., 70% humidity. The granules having the flexible film exhibited, versus initial activity, 20.98% retained enzyme activity and the granules without the flexible film exhibited 20.52 retained enzyme activity. In another example under high stress storage conditions, glucoamylase granules with and without flexible gelatin film coatings were tested as above. The granules having the flexible film exhibited, versus initial activity, 92.25% retained activity and the granules without the flexible film exhibited 98.31% retained activity.

Stability tests also were conducted comparing elastic protease granules prepared by the process described in WO 01/25323 to protease granules having the sucrose core and a flexible gelatin film coating as described in Example 3. The results after three days of storage under the high stress conditions described above, versus initial activity, showed that the commercially available elastic granule retained only 1.28% activity as opposed to 18.78% retained activity for the granule with the flexible gelatin film coat.

Example 9

Enzyme Release

Enzyme granules with the impact resistant flexible film of the present invention released enzyme within 2 minutes in simulated wash conditions. Release was tested by adding a detergent solution (1 g/L WFK base) to a Tergotomer at 25° C. and operated at 75 rmps. Aliquots samples were removed using a syringe in combination with a 0.45 μm syringe filter in order to separate out any enzyme granules that had not dissolved. Enzymatic activity in the aliquots was determined by standard enzyme assays and the change in activity over time was used to calculate dissolution curves for: (a) granules without a flexible coating; (b) the granules of (a) with a gelatin flexible film coating; (c) the granules of a with (a) PVA flexible film coating; and (d) the granules of (a) with a modified starch flexible film coating. The results showed that at least approximately 80% of all of the granules, except the granule having a gelatin flexible film coating dissolved within 2 minutes. Approximately 70 to 75% of the granule with the gelatin flexible film coating dissolved within 2 minutes and 80% dissolution was achieved prior to 3 minutes.

Various other examples and modifications of the foregoing description and examples will be apparent to those skilled in the art after reading the disclosure without departing from the spirit and scope of the invention, and it is intended that all such examples or modifications be included within the scope of the appended claims. All publications and patents referenced herein are hereby incorporated by reference in their entirety.

What is claimed is:

1. A highly impact-resistant granule comprising a) an impact-sensitive particle including an active ingredient and b) a flexible film comprising a polymer surrounding said impact-sensitive particle, wherein said film has an elongation upon break of at least about 30% , determined by dividing gage length measured after breakage of the film due to applying tensile strain by original gage length of the film of 10–100 mm prior to applying tensile strain, and said film comprises less than about 20% by weight of the highly impact-resistant granule, wherein said impact-sensitive particle has more than about 10% mass attrition and said highly impact-resistant granule has less than about 5% mass attrition, wherein mass attrition is determined by a Repeated Impact Test (RIT), using 216,000 collisions at 8.7 m/s and an amplitude of 1.5 cm.

2. The granule of claim 1, wherein the polymer is selected from the group consisting of PVA, gelatin and modified starch.

3. The granule of claim 2, wherein the film further comprises a gelling agent.

4. The granule of claim 1, wherein the film comprises PVA, glycerol and a gelling agent.

5. The granule of claim 1, wherein the active ingredient is a protein or peptide.

6. The granule of claim 5, wherein the protein is an enzyme.

* * * * *